(12) United States Patent
Kaercher et al.

(10) Patent No.: US 12,029,402 B2
(45) Date of Patent: Jul. 9, 2024

(54) COUPLING DEVICE FOR A DISASSEMBLABLE MEDICAL INSTRUMENT

(71) Applicant: KARL STORZ GmbH & Co. KG, Tuttlingen (DE)

(72) Inventors: Daniel Kaercher, Radolfzell (DE); Robin Merz, Furtwangen (DE); Jochen Stefan, Wald (DE)

(73) Assignee: Karl Storz SE & CO. KG, Tuttlingen (DE)

( * ) Notice: Subject to any disclaimer, the term of this patent is extended or adjusted under 35 U.S.C. 154(b) by 770 days.

(21) Appl. No.: 15/368,793

(22) Filed: Dec. 5, 2016

(65) Prior Publication Data

US 2017/0164936 A1 Jun. 15, 2017

(30) Foreign Application Priority Data

Dec. 10, 2015 (DE) ...................... 10 2015 121 481.4

(51) Int. Cl.
*A61B 17/00* (2006.01)
*A61B 17/29* (2006.01)
*A61B 90/00* (2016.01)

(52) U.S. Cl.
CPC .... *A61B 17/00234* (2013.01); *A61B 17/2909* (2013.01); *A61B 2017/00345* (2013.01); *A61B 2017/00367* (2013.01); *A61B 2017/00464* (2013.01); *A61B 2017/00526* (2013.01); *A61B 2017/292* (2013.01); *A61B 2090/0813* (2016.02)

(58) Field of Classification Search
None
See application file for complete search history.

(56) References Cited

U.S. PATENT DOCUMENTS

| 5,009,661 A | * | 4/1991 | Michelson | ......... | A61B 17/1608 606/170 |
|---|---|---|---|---|---|
| 5,290,309 A | | 3/1994 | Kothe | | |
| 5,342,391 A | | 8/1994 | Foshee et al. | | |

(Continued)

FOREIGN PATENT DOCUMENTS

| DE | 103 28 515 A1 | 1/2005 |
|---|---|---|
| DE | 20 2009 013 504 U1 | 2/2010 |

(Continued)

*Primary Examiner* — Erica S Lee
(74) *Attorney, Agent, or Firm* — Muncy, Geissler, Olds & Lowe, P.C.

(57) ABSTRACT

Handling device for the formation of a disassemblable medical instrument comprises a first component, a second component, which can be moved relative to the first component, a coupling device on the second component, wherein the coupling device is designed and arranged in order to be coupled to a corresponding coupling device at the proximal end of a force transmission device within a working range of positions of the second component and in order not to be coupled to a corresponding coupling device at the proximal end of a force transmission device in a release position of the second component, and a guiding device on the first component for guiding a corresponding coupling device at the proximal end of a force transmission device within a transitional range between one end of the working range and the release position.

10 Claims, 6 Drawing Sheets

(56) References Cited

U.S. PATENT DOCUMENTS

| | | | |
|---|---|---|---|
| 5,507,297 A * | 4/1996 | Slater | A61B 17/29 |
| | | | 600/564 |
| 5,718,714 A | 2/1998 | Livneh | |
| 8,876,805 B2 | 11/2014 | Kaercher et al. | |
| 2012/0259358 A1 | 10/2012 | Kaercher et al. | |
| 2014/0155933 A1 | 6/2014 | Stefan et al. | |
| 2016/0120595 A1 * | 5/2016 | Motai | A61B 18/1447 |
| | | | 606/47 |

FOREIGN PATENT DOCUMENTS

| | | |
|---|---|---|
| DE | 10 2011 007 119 A1 | 10/2012 |
| DE | 10 2012 200 073 A1 | 7/2013 |
| DE | 10 2012 022 573 A1 | 5/2014 |
| EP | 0 513 471 A2 | 11/1992 |
| EP | 1 622 521 B1 | 1/2011 |

* cited by examiner

Fig. 3
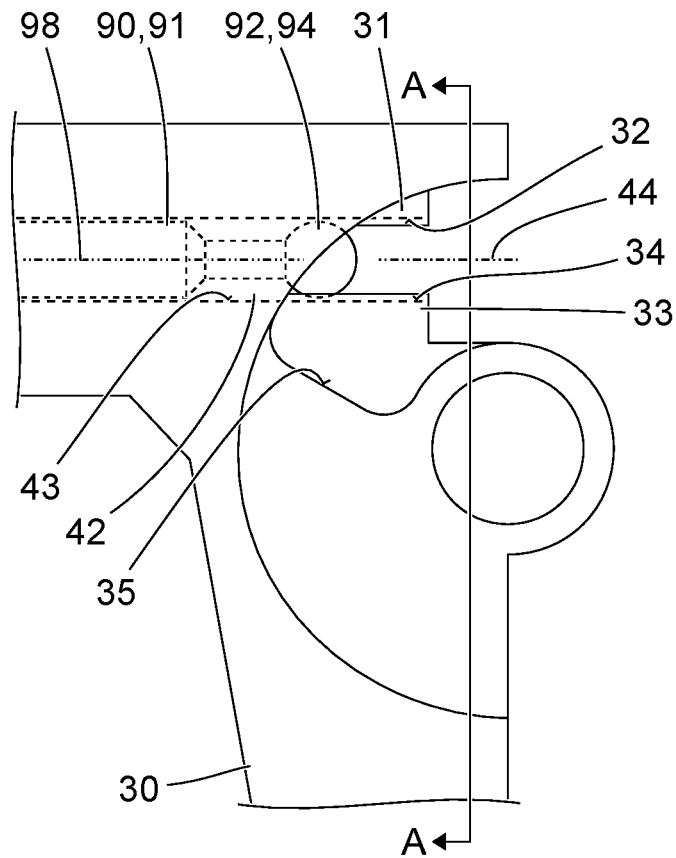
Fig. 4   A-A
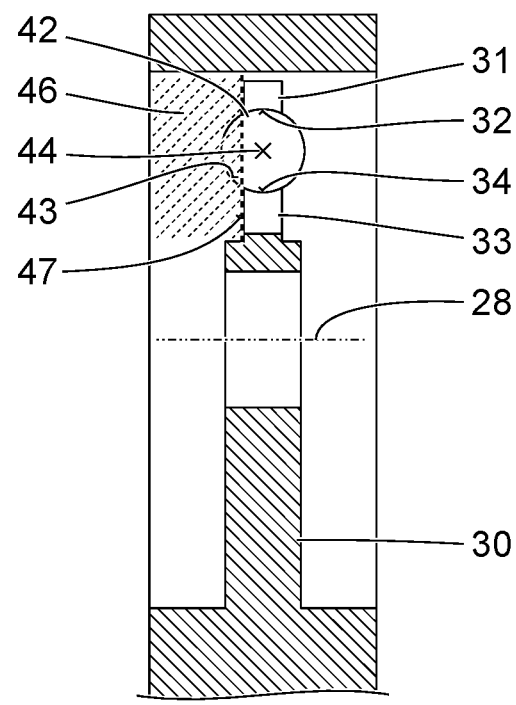

Fig. 5   B-B
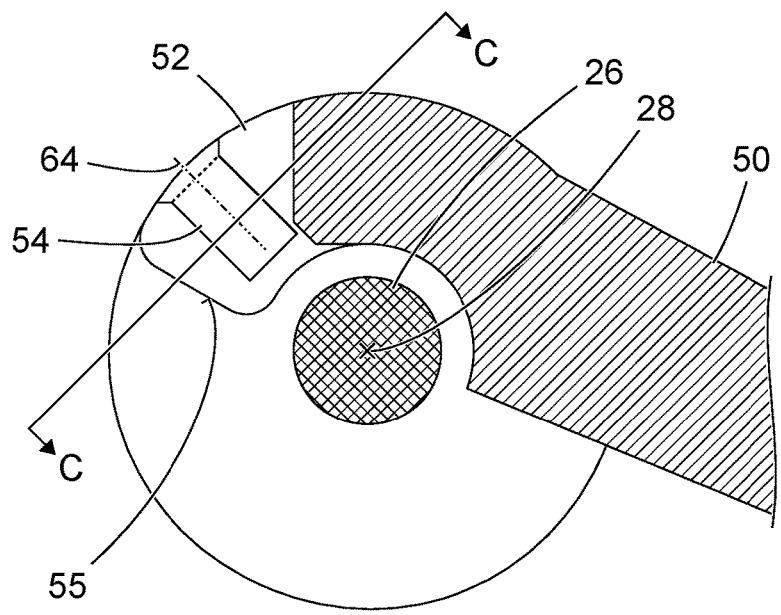
Fig. 6   C-C
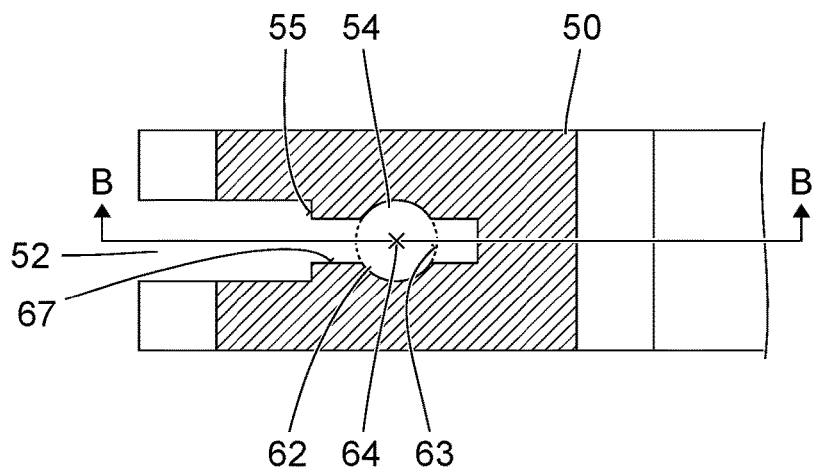

COUPLING DEVICE FOR A DISASSEMBLABLE MEDICAL INSTRUMENT

This nonprovisional application claims priority under 35 U.S.C. § 119(a) to German Patent Application No. 10 2015 121 481.4, which was filed in Germany on Dec. 10, 2015.

BACKGROUND OF THE INVENTION

Field of the Invention

The present invention relates to a handling device for the formation of a disassemblable medical instrument and to a disassemblable medical instrument wherein the disassemblable medical instrument is, in particular, a disassemblable medical instrument for microinvasive procedures.

Description of the Background Art

Reusable medical instruments must be fully cleaned and sterilized after each use. The possibility of complete disassembly of a medical instrument can significantly simplify cleaning or even make extensive or complete cleaning possible in the first place. Moreover, the possibility of disassembly can allow a combination of different handling devices with different shanks and different tools, for example (e.g. scissors, pincers, needle holders).

With many medical instruments for microinvasive procedures, a distal end of a shank can be connected mechanically in a releasable manner to a tool and a proximal end of the shank can be connected mechanically in a releasable manner to a handling device. A pull rod or some other force transmission device is arranged in the shank. The distal end of the force transmission device is coupled mechanically (and often connected permanently) to the tool. In the assembly of the medical instrument, the proximal end of the force transmission device is guided through a bore in a first component of the handling device, for example, and coupled mechanically to a second component of the handling device, which can be moved relative to the first component.

Progressive miniaturization of microinvasive medical instruments is leading to ever smaller cross sections and hence to decreasing mechanical robustness. Particularly during the assembly of a microinvasive medical instrument, the proximal end of a force transmission device can easily be bent, for example.

Alternative concepts for the releasable mechanical coupling of a proximal end of a force transmission device are described in DE 10 2011 007 119 A1, in DE 10 2012 022 573 A1 and in DE 10 2012 200 073 A1. However, these concepts are not suitable for all uses. In particular, they require an overall volume which is not available or should not be made available in all cases.

SUMMARY OF THE INVENTION

It is an object of the present invention to provide an improved handling device for the formation of a disassemblable medical instrument, an improved disassemblable medical instrument and an improved method for producing a handling device.

Embodiments of the present invention are based on the concept of providing, on a handling device, a guiding and/or supporting device which guides or supports the proximal end of a force transmission device during the coupling process and thus prevents deformation of the proximal end of the force transmission device.

A handling device for the formation of a disassemblable medical instrument comprises a first component, a second component, which can be moved relative to the first component, a coupling device on the second component, which coupling device is designed and arranged in order to be coupled to a corresponding coupling device at the proximal end of a force transmission device within a working range of positions of the second component and in order not to be coupled to a corresponding coupling device at the proximal end of a force transmission device in a release position of the second component, and a guiding device on the first component for guiding a corresponding coupling device at the proximal end of a force transmission device within a transitional range between one end of the working range and the release position.

The handling device is provided and designed in order to form, together with one or more additional components, a medical instrument which can be disassembled without destruction and in a reversible manner, that is to say can easily be reassembled again so as to be functional. The additional components comprise, for example, a shank, scissors, pincers, a needle holder or some other tool which is connected or can be connected to the distal end of the shank, and a force transmission device. The force transmission device is arranged within the shank or provided for arrangement within the shank. The distal end of the force transmission device can be connected mechanically to the tool in a nondetachable manner or a manner which does not allow it to be detached without destruction. The force transmission device is provided and designed to transmit a force (parallel to the longitudinal direction of the force transmission device) and/or of a torque. In particular, the force transmission device is a pull rod made of metal or some other material with a low elongation elasticity. In particular, the force transmission device is coupled to the tool in such a way that movement of the force transmission device in a proximal direction is associated with closure, gripping or a cutting movement of the tool.

In particular, the handling device is provided and designed for a—or for the formation of a—disassemblable medical instrument for microinvasive uses.

In particular, the first component and the second component are designed and arranged in such a way that they can be moved relative to one another with one hand by a medical worker. The handling device can have a plurality of second components or more than two components that can be moved relative to one another.

The first component can be monolithic or can be assembled from two or more elements. In particular, the first component is connected mechanically in a permanent way or can be connected mechanically in a releasable manner to the proximal end of a shank. In particular, the first component is connected or can be connected to the proximal end of a shank in such a way that the shank cannot be moved relative to the first component or can be rotated relative to the first component only about its longitudinal axis. In particular, the first component has a lug or a gripping opening for one or more fingers of a human hand.

The second component can be monolithic or assembled from a plurality of elements. The second component is pivotable relative to the first component, in particular about a pivoting axis defined by a shaft or in some other way. As an alternative or in addition, the second component can be moved relative to the first component along a straight or curved path or can be moved in several directions in space.

In particular, the second component has a lug or a gripping opening for one or more fingers of a human hand.

The working range comprises a plurality of positions of the second component relative to the first component, which are provided for the intended use of the handling device as part of a disassemblable medical instrument. Owing to the mechanical coupling of the second component to a tool via the force transmission device, a movement of the second component is associated with a movement of the tool, and for each position of the second component relative to the first component there is a corresponding configuration or position of the tool.

In particular, the working range comprises a first extreme position of the second component relative to the first component, which is associated with a completely closed configuration of pincers or a needle holder or a scissor configuration at the end of a cutting process at the distal end of the disassemblable medical instrument. In particular, the working range furthermore comprises a second extreme position, which is associated with a completely open configuration of pincers or a needle holder or a scissor configuration at the beginning of a cutting process at the distal end of the disassemblable medical instrument. In particular, the working range furthermore comprises all positions between the two extreme positions described within the working range.

The release position of the second component relative to the first component can be positively defined by a stop or by two surfaces on the first component and the second component, which are arranged opposite one another and touch one another in the release position. In the release position of the second component relative to the first component, the handling device is in a configuration in which the coupling device on the second component is not coupled or cannot be coupled to a corresponding coupling device at the proximal end of a force transmission device. However, the coupling device on the second component can be coupled to a corresponding coupling device at the proximal end of a force transmission device by moving the second component relative to the first component in the transitional range toward the working range from the release position. By means of a reverse motion of the second component from one end of the working range, through the transitional range, toward the release position, the coupling device on the second component can be separated from a corresponding coupling device at the proximal end of a force transmission device.

The coupling device on the second component and a corresponding coupling device at the proximal end of the force transmission device may be designed in order, in an idealized, in particular frictionless, case, to allow a clear distinction between two directly adjoining ranges in which there is coupling or no coupling, wherein the boundary between the two ranges can be formed by the release position or can be close to the release position. In reality, static friction between surfaces which are supposed to slide on one another, in particular, can have the effect that a movement of the second component relative to the first component is not associated with an intended longitudinal movement of the force transmission device, for example, but, instead, the proximal end of the force transmission device is subject to a force orthogonal to the longitudinal direction and is bent in the process. The guiding device can guide and support the proximal end of a force transmission device, at least in part of the transitional range. The guiding device can therefore absorb unanticipated forces which are not parallel to the longitudinal direction of the force transmission device and can thus prevent deformation of the proximal end of the force transmission device.

In the case of a handling device of the kind described here, the guiding device is, in particular, designed and arranged in order to guide a corresponding coupling device at the proximal end of a force transmission device within the entire transitional range.

Guidance of the proximal end of a force transmission device within the entire transitional range between the release position and that end of the working range which is adjacent to the release position can prevent deformation and damage of the force transmission device.

In the case of a handling device of the kind described here, the guiding device is, in particular, designed and arranged in order to guide a corresponding coupling device at the proximal end of a force transmission device at one position within the working range.

In particular, the guiding device is designed and arranged in order to guide a corresponding coupling device at the proximal end of a force transmission device within one part of the working range or within the entire working range. Particularly in the case of pivotability of the second component, guiding the proximal end of a force transmission device not only within the transitional range but also within part of the working range or the entire working range can prevent deformation of the proximal end of a force transmission device.

In the case of a handling device of the kind described here, the guiding device comprises, in particular, a sliding surface for guiding a corresponding coupling device at the proximal end of a force transmission device.

In particular, the sliding surface is invariant in respect of translation or cylinder-symmetrical or parallel to the envisaged direction of motion of the corresponding coupling device. In particular, the sliding surface is arranged in such a way that it touches the surface of a corresponding coupling device at the proximal end of a force transmission device in every envisaged position of said coupling device without exerting a force or having a small clearance from the surface thereof. A clearance between the sliding surface of the guiding device and a surface of a corresponding coupling device at the proximal end of a force transmission device is small if a deformation of the force transmission device which does not cause plastic or permanent deformation of the force transmission device is required for contact between the sliding guide and the surface.

In particular, the sliding surface is designed and arranged in such a way that the central surface normal thereof is parallel or substantially parallel to a direction of a force which the second component can exert on a coupling device at the proximal end of a force transmission device.

In the case of a handling device of the kind described here, the sliding surface is, in particular, arranged at one edge of a web on the first component.

In particular, the web has the form of a segment of a flat plate. In particular, the web is parallel or substantially parallel to a central surface normal of the sliding surface.

In the case of a handling device of the kind described here, the second component has, in particular, a slot, in which the web on the first component is arranged.

In the case of a handling device of the kind described here, the coupling device on the second component comprises, in particular, two parallel and mutually opposite grooves in two mutually opposite walls of the slot.

In particular, the grooves are arranged in such a way that they can guide a corresponding coupling device at the proximal end of a force transmission device along a predetermined path relative to the second component with little play and little friction. In particular, the grooves and the path are straight. In the case of pivotability of the second component, the grooves are arranged radially with respect to the pivoting axis, for example. In particular, the grooves are designed and arranged in such a way that, in the release position of the second component relative to the first component, a corresponding coupling device at the proximal end of a force transmission device can be arranged at first ends of the grooves or can be introduced into first ends of the grooves. By means of movement of the second component relative to the first component away from the release position and toward the working range or within the working range, a coupling device at the proximal end of a force transmission device can be moved both along the guiding device relative to the first component and simultaneously along the grooves relative to the second component.

In the case of a handling device of the kind described here, the sliding surface has, in particular, the form of a segment of a lateral surface of a circular cylinder.

A sliding surface in the form of a segment of a lateral surface of a circular cylinder can be formed as part of an inner surface of a bore, for example. In particular, the sliding surface is the continuation of an inner surface of a bore into which a force transmission device is introduced from the distal side toward the proximal side as a disassemblable medical instrument is put together or assembled and through which a coupling device at the proximal end of the force transmission device can be passed.

In the case of a handling device of the kind described here, the width of the web and the width of the slot, in particular, are each less than the width of the corresponding coupling device at the proximal end of a force transmission device for which the handling device is provided.

In the case of a handling device of the kind described here, the coupling device is, in particular, designed for coupling to a spherical corresponding coupling device at the proximal end of a force transmission device, wherein the width of the web and the width of the slot are each less than the diameter of the spherical corresponding coupling device at the proximal end of a force transmission device for which the handling device is provided.

If the width of the web is less than the diameter of the spherical corresponding coupling device, the spherical corresponding coupling device protrudes beyond the web on one side or on both sides. If the width of the slot is less than the diameter of the spherical corresponding coupling device, the spherical corresponding coupling device can engage in a groove in an inner wall of the slot or can engage simultaneously in two mutually opposite grooves in two mutually opposite walls of the slot. The spherical corresponding coupling device can thus be guided simultaneously relative to the first component by the web or the sliding surface on the web and relative to the second component by the groove or grooves on the inner surface of the slot.

In the case of a handling device of the kind described here, the guiding device comprises, in particular, two mutually opposite sliding surfaces, which are designed and arranged in order to guide between them a corresponding coupling device at the proximal end of a force transmission device.

In particular, the cross section of the space bounded by the two mutually opposite sliding surfaces is only slightly larger than the cross section of the corresponding coupling device at the proximal end of the force transmission device for which the handling device is provided in order to allow guidance with little play and little friction. In particular, the two sliding surfaces lie opposite one another in a direction which is parallel to a plane in which the second component is situated. In particular, the two sliding surfaces lie opposite one another in a direction which is orthogonal to a pivoting axis about which the second component can be pivoted.

In the case of a handling device of the kind described here, the sliding surfaces have, in particular, the form of two segments of a lateral surface of a circular cylinder.

In particular, the sliding surfaces are formed by segments or regions of an inner surface of a bore in the first component.

A handling device of the kind described here furthermore comprises, in particular, a shank coupling device for the releasable mechanical connection of the handling device to a proximal end of a shank.

A disassemblable medical instrument comprises a handling device of the kind described here, a shank, the proximal end of which is connected or can be connected mechanically in a releasable manner to the handling device, and a force transmission device having a coupling device, corresponding to the coupling device on the second component, at the proximal end of the force transmission device.

In a disassemblable medical instrument of the kind described here, the coupling device at the proximal end of the force transmission device is, in particular, spherical.

A method for producing a handling device for the formation of a disassemblable medical instrument comprises a step of producing a first bore in a first component, wherein the first bore is provided and designed to receive a proximal region of a force transmission device, a step of removing material from the first component on two opposite sides as far as two parallel flat surfaces, which are parallel to the axis of the first bore and intersect the inner surface of the first bore, a step of producing a second bore in a second component, wherein the second bore is provided and designed to receive a coupling device at the proximal end of a force transmission device, a step of producing a slot in the first component, wherein the slot is parallel to an axis of the second bore and wherein the width of the slot is less than the diameter of the second bore, and a step of connecting the first component and the second component in such a way that the second component can be moved relative to the first component.

In particular, the method is suitable for producing a handling device of the kind described here or for producing a handling device having features described here.

The steps can be carried out in some other sequence. In particular, the axis of the first bore is arranged between the two parallel flat surfaces up to which material is removed from the first component. In particular, the axis of the second bore is arranged within the slot in the second component. The first bore, the second bore and the slot can each be produced by means of a cutting method, by electroerosion, laser or water jet cutting or in some other way. Removing the material from the first component can also be accomplished by means of one of the stated methods.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 3 shows a schematic illustration of a component of the handling device from FIG. 2;

FIG. 4 shows a schematic sectional illustration of the component from FIG. 3;

FIG. 5 shows a schematic sectional illustration of another component of the handling device from FIG. 2;

FIG. 6 shows another schematic sectional illustration of the component from FIG. 5;

DETAILED DESCRIPTION

Figure 1:
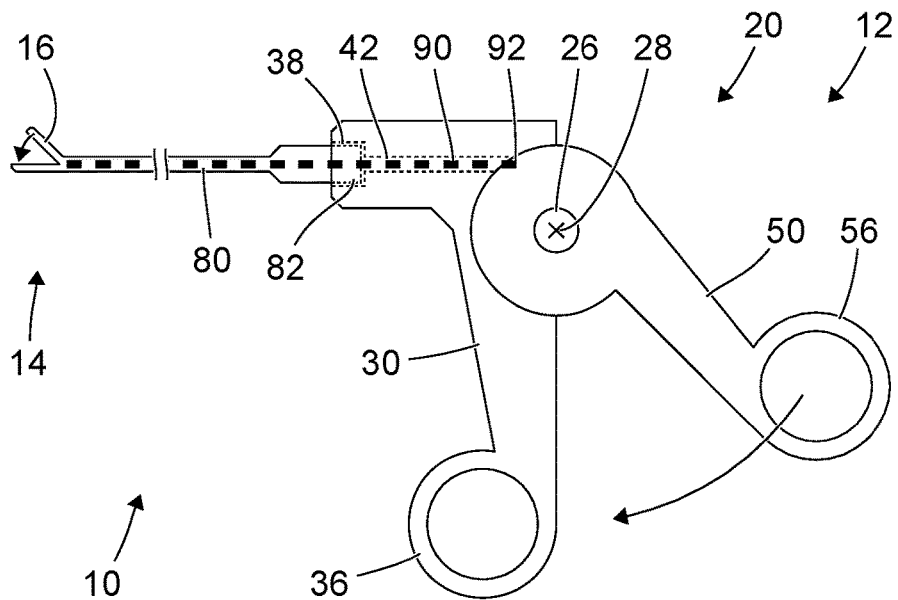
FIG. 1 shows a schematic illustration of a disassemblable medical instrument.

FIG. 1 shows a schematic illustration of a disassemblable medical instrument 10, which is provided and designed, in particular, for use in the context of a microinvasive procedure. The proximal end 12 of the medical instrument 10 is formed by a handling device 20. The distal end 14 is formed by a tool 16. A shank 80 extends from the handling device 20 to the tool 16. The tool 16 is a pair of scissors, pincers or a needle holder having two or more branches, of which at least one can be moved relative to the other and to the shank 80.

The handling device 20 comprises a first component 30 and a second component 50, which are connected to one another by a joint 26. The joint 26 defines a pivoting axis 28 orthogonal to the plane of the drawing in FIG. 1. The joint 26 is a short shaft, for example, which forms a sliding bearing with the first component 30 and is connected rigidly to the second component 50.

A lug or gripping opening 36 for one or more fingers of a human hand is arranged on the first component 30. A lug or gripping opening 56 for one or more fingers of a human hand is likewise arranged on the second component 50. The lug 36 on the first component 30 is provided for the middle finger, the ring finger or some other finger and the lug 56 on the second component 50 is provided for the thumb of the same hand, for example.

A recess 38 to accommodate the proximal end 82 of the shank 80 is provided on the first component 30. The recess 38 is indicated in simplified form as a blind hole in FIG. 1. By means of a locking device (not shown in FIG. 1), the proximal end 82 of the shank 80 can be held in the recess 38. As an extension of the recess 38, the first component 30 has a bore 42. The cross section of the bore 42 is smaller than the cross section of the recess 38.

A force transmission device 90—e.g. a pull rod—is arranged in the shank 80 and in bore 42. In FIG. 1, the force transmission device 90 is indicated by a wide broken line since it is arranged within the shank 80 and the first component 30 and is therefore not visible from the outside. The force transmission device 90 can be moved in a direction parallel to the longitudinal axis of the force transmission device 90 in the shank 80 and in bore 42. The force transmission device 90 comprises metal or some other material of low elongation elasticity, for example. In particular, the force transmission device 90 has a small cross section and therefore a high flexural elasticity. As an option, the force transmission device 90 can additionally be provided and designed to transmit a torque or a rotary motion from the handling device 20 to the tool 16.

As shown by means of FIGS. 2 to 10, the proximal end 92 of the force transmission device 90 is coupled to the second component 50, with the result that a movement of the second component 50 is associated with a movement of the force transmission device 90. The distal end of the force transmission device 90 is coupled to the tool 16 at the distal end 14 of the medical instrument 10 in such a way that a movement of the force transmission device 90 is associated, for example, with a pivoting movement of a pivotable branch or of two pivotable branches of the tool 16.

In the illustrated example, the second component 50 at the proximal end 92 of the force transmission device 90 as well as the distal end of the force transmission device 90 and the tool 16 are coupled in such a way that a pivoting movement of the second component 50 toward the first component 30 is associated with a gripping movement or a cutting movement of the tool 16 at the distal end 14 of the medical instrument 10.

The medical instrument 10 can be disassembled without destruction and in a reversible manner. In particular, the handling device 20 can be separated from the proximal end 82 of the shank 80. For this purpose, starting from the situation shown in FIG. 1, a push button for unlocking the connection between the handling device 20 and the shank 80 is pressed and, at the same time or after this, the proximal end 82 of the shank 80 is pulled out of the recess 38 in the first component 30 in the distal direction, for example. During this process, the force transmission device 90, including the proximal end 92 thereof, is, in particular, simultaneously also pulled out of the bore 42 in the first component 30 in the distal direction. Furthermore, the shank 80 and the tool 16 can be connected to one another mechanically in a nondestructively and reversibly releasable manner. The distal end of the force transmission device 90 can be permanently connected to the tool 16.

Figure 2:
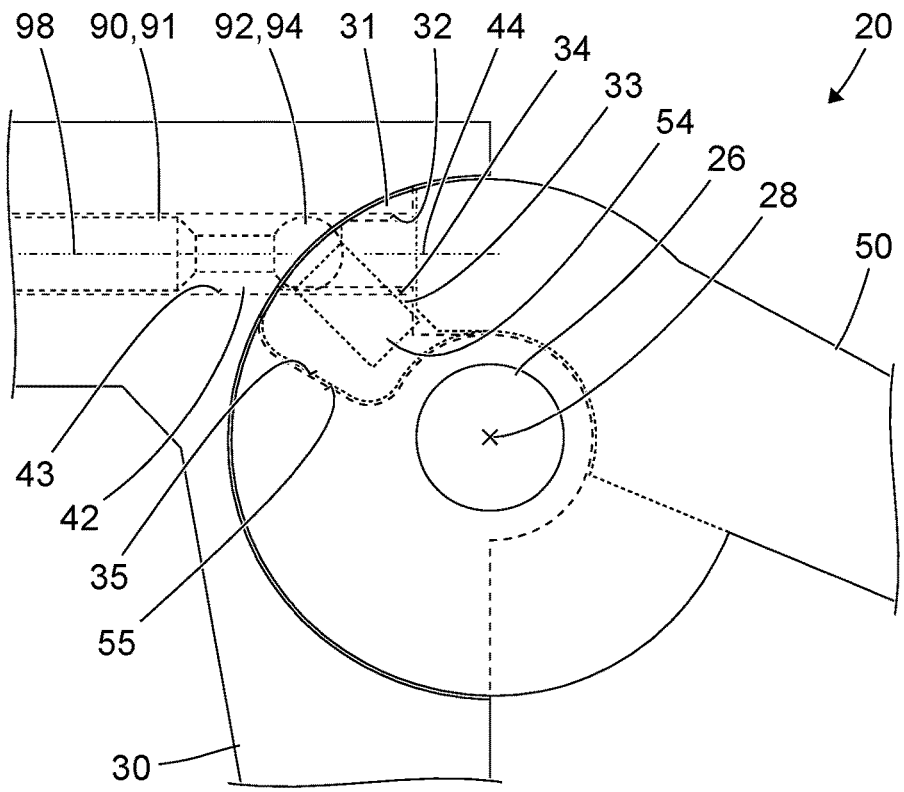
FIG. 2 shows a schematic illustration of parts of the handling device for the medical instrument from FIG. 1.

FIG. 2 shows a schematic illustration of parts of the second first component 30 and of the second component 50 of a handling device 20 for a medical instrument of the kind illustrated, for example, by means of FIG. 1. The plane of the drawing in FIG. 2 corresponds to the plane of the drawing in FIG. 1. In FIG. 2, in contrast to FIG. 1, not only are externally visible features shown—in solid lines—but also—in broken lines—structures and features within the handling device 20 which are not visible from the outside. In particular, the handling device 20 is mirror-symmetrical or substantially mirror-symmetrical with respect to a plane of symmetry, which is parallel to the plane of the drawing in FIG. 2.

Like the handling device illustrated by means of FIG. 1, the handling device 20 shown in FIG. 2 also has a first component 30 and a second component 50. The handling device 20 comprises a joint 26, which defines a pivoting axis 28 orthogonal to the plane of the drawing in FIG. 2. In FIG. 2 only regions of the first component 30 and of the second component 50 close to the joint 26 are illustrated. The joint 26 is formed by a shaft or a pin which is circular-cylindrical or circular-cylindrical in some section or sections, which is guided in the first component with little play and little friction and is connected rigidly to the second component 50. The joint 26 allows a pivoting movement of the second component 50 relative to the first component 30 about the pivoting axis 28.

The first component 30 has a circular-cylindrical bore 42, into which a proximal region 91 of a force transmission device 90 has already been inserted in the situation shown in FIG. 2. The proximal end 92 of the force transmission device 90 is formed by a spherical or substantially spherical coupling device 94. The cross section of the bore 42 and the cross sections of the force transmission device 90, including the coupling device 94 at the proximal end 92 of the force transmission device 90, are matched to one another in such a way that the force transmission device 90 is guided with little play and little friction by the inner surface 43 of the bore 42 and can be moved parallel to the axis of symmetry 98 thereof in the bore 42.

At its end facing the first component 30, the second component 50 has a slot which extends parallel to the plane of the drawing in FIG. 2. Parts of the first component 30 are arranged in the slot, and therefore the second component 50 is arranged partially in front of and partially behind those parts of the first component 30 which are arranged in the slot in the direction of view in FIG. 2.

In particular, a first web 31 and a second web 33 on the first component 30 are arranged in the slot mentioned in the second component 50. A first sliding surface 32 on the straight edge of the first web 31, which faces the second web 33, and a second sliding surface 34 on the straight edge of the second web 33, which faces the first web 31, form a guiding device for the coupling device 94 at the proximal end 92 of the force transmission device 90 in positions which are proximal to the position of the force transmission device 90 shown in FIG. 2.

In particular, the sliding surfaces 32, 34 have the form of two segments of a lateral surface of a circular cylinder with the axis of symmetry 44 and are therefore each concave. In particular, the sliding surfaces 32, 34 are smooth extensions of the inner surface 43 of the bore 42 in the proximal direction. The axis of symmetry 44 of the sliding surfaces 32, 34 is thus identical with the axis of symmetry 98 of the force transmission device 90.

Steps 35 are provided on the first component 30, and steps 55 are provided on the second component 50. In particular, two steps 35 are arranged on the first component 30 parallel and in mirror symmetry with respect to one another on a side facing the observer and on a side of the first component 30 facing away from the observer. In particular, two steps 55 are arranged on the second component 50 parallel and in mirror symmetry with respect to one another on two mutually opposite walls of the slot mentioned. In particular, the second web 33 extends from the steps 35 as far as the second sliding surface 34.

In the position of the second component 50 relative to the first component 30 shown in FIG. 2, the steps 55 on the second component 50 rest against the steps 35 on the first component 30. The steps 35 on the first component and the steps 55 on the second component 50 thus form a mechanical stop, which, by positive engagement, defines the release position, shown in FIG. 2, of the second component 50 relative to the first component 30 with a maximum angular spacing between the second component 50 and the first component 30.

Two parallel and mutually opposite grooves 54 are provided in two parallel and mutually opposite walls which delimit the mentioned slots in the second component 50. The cross sections of the grooves 54 are chosen in such a way that they can accommodate mutually opposite regions of the coupling device 94.

In the release position, illustrated in FIG. 2, of the second component 50 relative to the first component 30, the coupling device 94 at the proximal end 92 of the force transmission device 90 is at the open ends of the grooves 54. Starting from this situation or configuration, the force transmission device 90 can be pushed in the proximal direction. During this process, the second component 50 is pivoted clockwise about the pivoting axis 28, and the coupling device 94 slides into the grooves 54.

FIG. 3 shows a schematic illustration of the first component 30 of the handling device 20 illustrated by means of FIG. 2. The plane of the drawing in FIG. 3 corresponds to the plane of the drawing in FIG. 2. In contrast to the illustration in FIG. 2, only the first component 30, not the second component 50, is illustrated in FIG. 3. The webs 31, 33 and step 35 are therefore visible. The sliding surfaces 32, 34 on the mutually facing edges of the webs 31, 33 are concave and are therefore also not visible in the illustration in FIG. 3 and are indicated only by a broken lines.

FIG. 4 shows a schematic illustration of a section along the plane A-A, indicated in FIG. 3, through the first component 30. Section plane A-A is orthogonal to the planes of the drawings of FIGS. 2 and 3 and orthogonal to the axis of symmetry 44 of the sliding surfaces 32, 34.

Since the sliding surfaces 32, 34 are straight and flat extensions of the inner surface 43 of the bore 42 in the first component 30, the axis of symmetry 44 of the sliding surfaces 32, 34 is simultaneously the axis of symmetry of the inner surface 43 of the bore 42. In particular, the sliding surfaces 32, 34 are produced simultaneously or in the same operation with the bore 42. The diameter of the bore 42 corresponds substantially to the diameter of the coupling device 94 at the proximal end 92 of the force transmission device 90 (cf. FIG. 3). The diameter of the bore 42 is larger than the thickness of the webs 31, 33, measured in a direction parallel to the pivoting axis 28.

In the production of the first component 30, material is removed symmetrically or substantially symmetrically from two mutually opposite sides, in particular after the production of bore 44 as a through hole. Inter alia, material is removed in two spatial regions 46 that are mirror-symmetrical with respect to one another, one of which is shown hatched in broken lines in FIG. 4. The two mirror-symmetrical spatial regions 46 are delimited by flat surfaces 47, which are arranged in mirror symmetry and of which one is indicated by a straight broken line in FIG. 4. The flat surfaces 47 up to which material is removed intersect the cross section of bore 42. Therefore, only the strip-shaped concave sliding surfaces 32, 34 remain of the inner surface of bore 42 after the removal of material in the spatial regions 46. The flat surfaces 47 each simultaneously form two surface regions facing away from one another on the webs 31, 33.

FIG. 5 shows a schematic illustration of a section through the second component 50 of the handling device illustrated by means of FIG. 2 along a section plane B-B. Section plane B-B is parallel to the planes of the drawings of FIGS. 1 to 3 and is simultaneously the plane of symmetry with respect to which the second component 50 is mirror-symmetrical or substantially mirror-symmetrical.

Section plane B-B is situated in the mentioned slot 52 in the second component 50. The shaft or pin which forms the joint 26 passes through the slot orthogonally. This leaves a slot shape which, in a mathematical sense, is biconnected and homeomorphous with respect to a ring.

The slot 52 has different widths in two regions separated by step 55 (as measured in a direction parallel to the pivoting axis 28 and orthogonally to section plane B-B). In a region in which the slot 52 has a smaller width, there is a respective groove 54 arranged on each of the mutually facing and opposite walls of the slot 52. The grooves 54 are parallel to one another and have inner surfaces which have substantially the form of two segments of the lateral surface of a circular cylinder with the axis of symmetry 64. As a departure from this, chamfers or funnel-shaped entries are provided on the ends of the grooves 54 which are radially on the outside or remote from the joint 26.

FIG. 6 shows a schematic illustration of a section along the section plane C-C, indicated in FIG. 5, through the second component 50 illustrated by means of FIGS. 2 and 5. Section plane C-C is orthogonal to section plane B-B in FIG. 5, parallel to the pivoting axis 28 and orthogonal to the axis of symmetry 64 of the grooves 54. The position of section plane B-B in FIG. 5, with respect to which the second component 50 is mirror-symmetrical, is indicated in FIG. 6.

In FIG. 6, it can be seen that the slot 52 has two regions of different widths, between which the steps 55 are arranged. The surface normals of the steps 55 are parallel to section plane B-B in FIG. 5 and orthogonal to the pivoting axis 28 (cf. FIGS. 2 and 5).

The grooves 54 are produced by producing a bore 62, the axis of symmetry of which corresponds to the axis of symmetry 64 of the grooves 54, in particular simultaneously and before the production of the slot 52. The axis of symmetry 64 of bore 62 and of the grooves 54 lies in the plane of symmetry of the second component 50 or in section plane B-B in FIG. 5. The slot 52 is delimited in the vicinity of the grooves 54 by two parallel and mutually opposite surfaces 67, the spacing between which is smaller than the diameter of bore 62. Of the inner surface 63 of bore 62, the production of the slot 52 leaves only the concave surfaces of the grooves 54.

Figure 7:
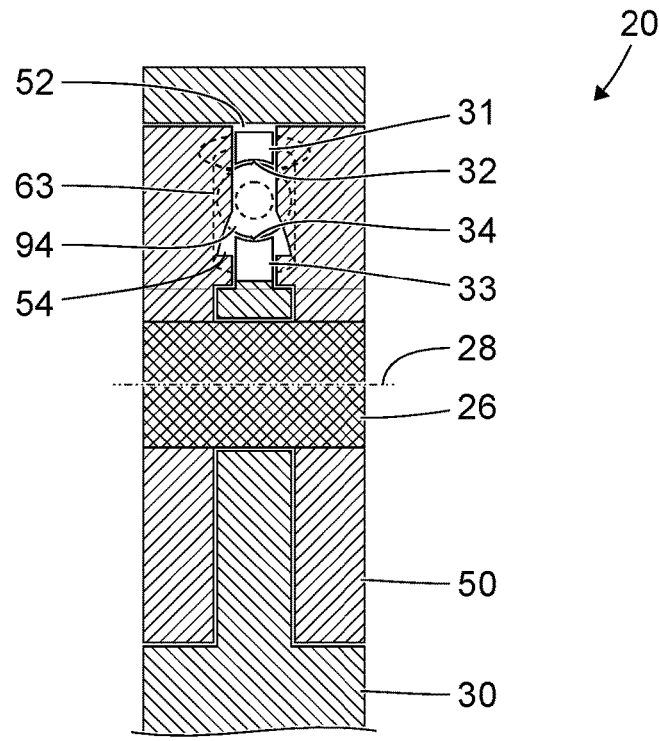
FIG. 7 shows another schematic sectional illustration of the handling device from FIG. 2.

FIG. 7 shows a schematic illustration of a section along section plane D-D through the handling device 20 illustrated by means of FIGS. 2 to 6. Section plane D-D corresponds to section plane A-A in FIG. 4. FIG. 7 shows a configuration or angular position of the second component 50 relative to the first component 30, which differs from that illustrated by means of FIG. 2, and which is described with reference to FIG. 8.

The grooves 54 are just intersected by section plane D-D. Contours of the concave surfaces of the grooves 54 which are not visible in the section illustrated are indicated by broken lines in FIG. 7.

The widths of the webs 31, 33 correspond largely to the width of the groove 52 in the vicinity of the grooves 54, with the result that the webs 31, 33 on the first component 30 are guided with little friction in the slot 52 in the second component 50. The coupling device 94 at the proximal end of the force transmission device is wider than the webs 31, 33 on the first component 30 and the slot 52 in the second component 50. The coupling device 94 engages in the grooves 54 in the second component 50. The sliding surfaces 32, 34 guide and support the coupling device 94 by positively preventing deflection of the coupling device 94 in a direction in section plane D-D.

Figure 8:
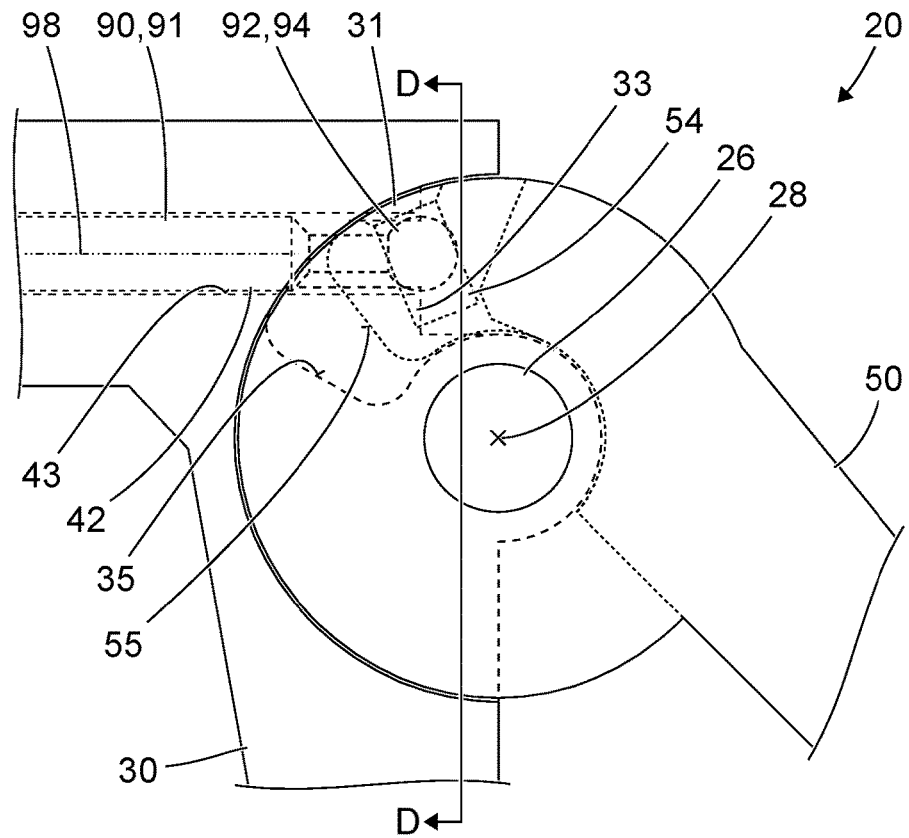
FIG. 8 shows another schematic illustration of the handling device from FIGS. 2 and 7.

FIG. 8 shows another schematic illustration of the handling device 20 illustrated by means of FIGS. 2 to 7. The plane of the drawing and the manner of illustration correspond to those in FIG. 2. However, FIG. 8 shows a situation or configuration which is also shown in FIG. 7 and which differs from that shown in FIG. 2. The section plane D-D in FIG. 7 is indicated in FIG. 8.

In the configuration shown in FIG. 8, the second component 50 has been pivoted through a predetermined angle toward the first component 30 from the release position shown in FIG. 2. Accordingly, the step 55 on the second component 50 is spaced apart from the step 35 on the first component 30. The position of the second component 50 shown in FIG. 8 lies at the end of a working range of positions which is close to the release position shown in FIG. 2, for example. The working range is formed by all the positions which are envisaged for the intended use of the handling device 20 as part of a medical instrument. The intended use is use in a medical procedure and does not include the disassembly, cleaning, sterilization, assembly and storage of the medical instrument between two uses in medical procedures.

The coupling device 94 at the proximal end 92 of the force transmission device 90 has been introduced completely into the grooves 54 in the second component 50 and is simultaneously situated in the outermost proximal position, in which it is still guided by the sliding surfaces on the webs 31, 33. Within the entire transitional range between the release position illustrated in FIG. 2 and the position illustrated in FIG. 8 at one end of the working range, the coupling device 94 at the proximal end 92 of the force transmission device 90 is guided and supported by the sliding surfaces 32, 34.

Figure 9:
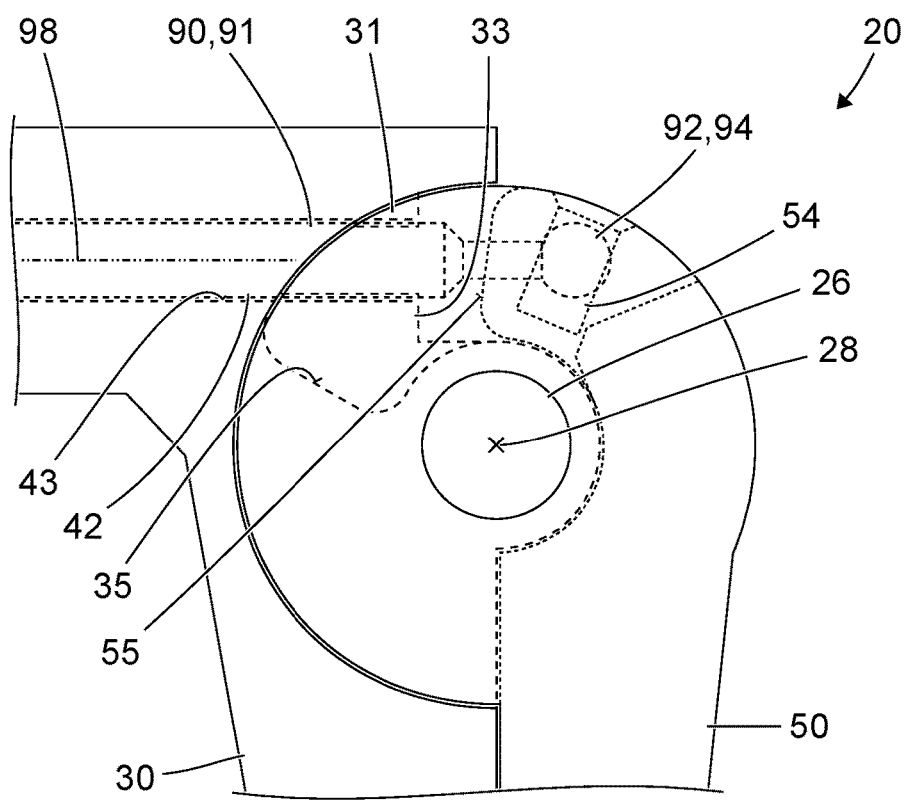
FIG. 9 shows another schematic illustration of the handling device from FIGS. 2, 7 and 8.

FIG. 9 shows another schematic illustration of the handling device 20 illustrated by means of FIGS. 2 to 8. The plane of the drawing and the manner of illustration correspond to those in FIGS. 2 and 8. However, the configuration or situation shown in FIG. 9 differs from those illustrated in FIGS. 2 and 8.

FIG. 9 illustrates a configuration or situation in which the second component 50 has been pivoted fully against the first component 30. This position of the second component 50 is at the opposite end of the working range from the position shown in FIG. 8. The coupling device 94 at the proximal end 92 of the force transmission device 90 is arranged in the grooves 54. Within the entire working range, which extends from the position of the second component 50 shown in FIG. 9 as far as the position of said component shown in FIG. 8 (or beyond said position), the coupling device 94 at the proximal end 92 of the force transmission device 90 engages in the grooves 54 in the second component 50. This engagement forms a positive coupling of the force transmission device 90 to the second component 50, with the result that a pivoting movement of the second component 50 about the pivoting axis 28 is associated with a translational movement of the force transmission device 90 in a direction parallel to the axis of symmetry 98 thereof.

By means of devices not illustrated in FIGS. 2 to 9, it is possible to ensure that the force transmission device 90 is moved distally beyond the position shown in FIG. 8 and hence that the second component 50 can be pivoted beyond the angular position shown in FIG. 8 as far as the release position shown in FIG. 2 only when there is simultaneous actuation of an unlocking element. In the release position shown in FIG. 2, the coupling device 94 at the proximal end 92 of the force transmission device 90 disengages from the grooves 54 in the second component 50, thus allowing the force transmission device 90 to be separated in the distal direction from the handling device 20 (in particular together with the shank 80—cf. FIG. 1). The position of the force transmission device 90 when the second component 50 is in the release position shown in FIG. 2 can correspond to a position beyond the open position of the tool 16 at the distal end 14 of the medical instrument (cf. FIG. 1).

Figure 10:
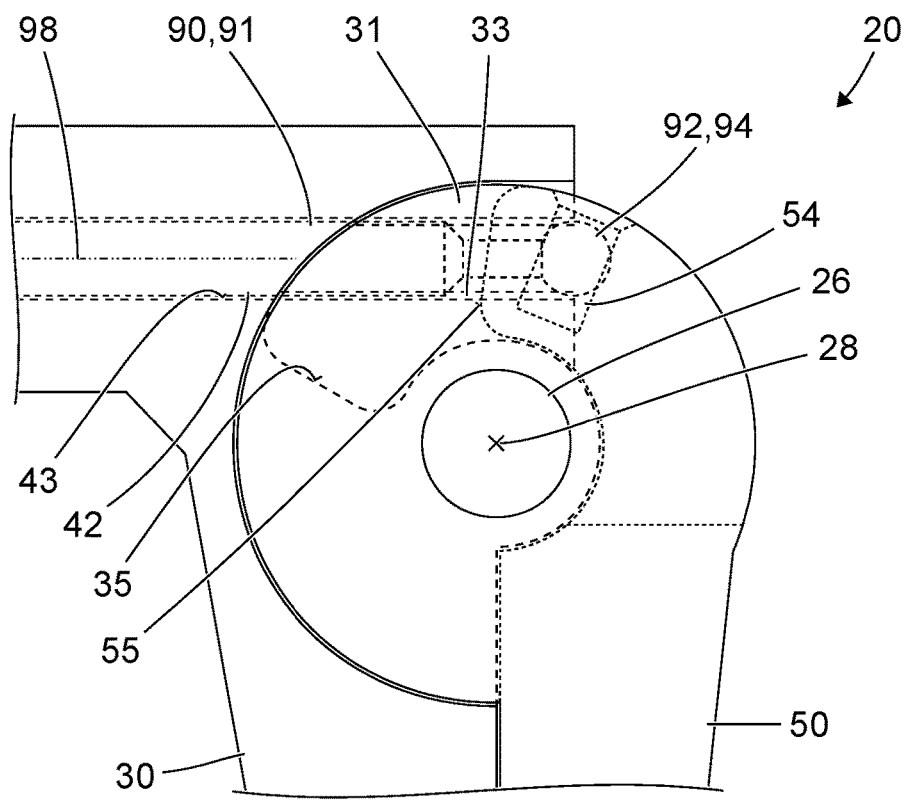
FIG. 10 shows a schematic illustration of another handling device.

FIG. 10 shows a schematic illustration of another handling device, which is similar in some features, characteristics and functions to the handling device 20 illustrated by means of FIGS. 2 to 9. The plane of the drawing and the manner of illustration correspond to those in FIGS. 2, 8 and 9.

The handling device 20 shown in FIG. 10 differs from the handling device illustrated by means of FIGS. 2 to 9, in particular, in that the webs 31, 33 extend significantly further in the proximal direction. In the example illustrated in FIG. 10, the webs 31, 33 and hence also the sliding surfaces 32, 34 on the mutually facing edges of the webs 31, 33 extend so far in the proximal direction that the coupling device 94 at the proximal end 92 of the force transmission device 90 is guided by the sliding surfaces on the webs 31, 33 over the entire working range, i.e. also in the position of the second component 50 shown in FIG. 10. Deformation of the force transmission device 90 is therefore excluded not only in the transitional range between the release position shown in FIG. 2 and the position at the edge of the working range, shown in FIG. 8, but also in the entire working range between the position shown in FIG. 8 and the position shown in FIGS. 9 and 10.

Figure 11:
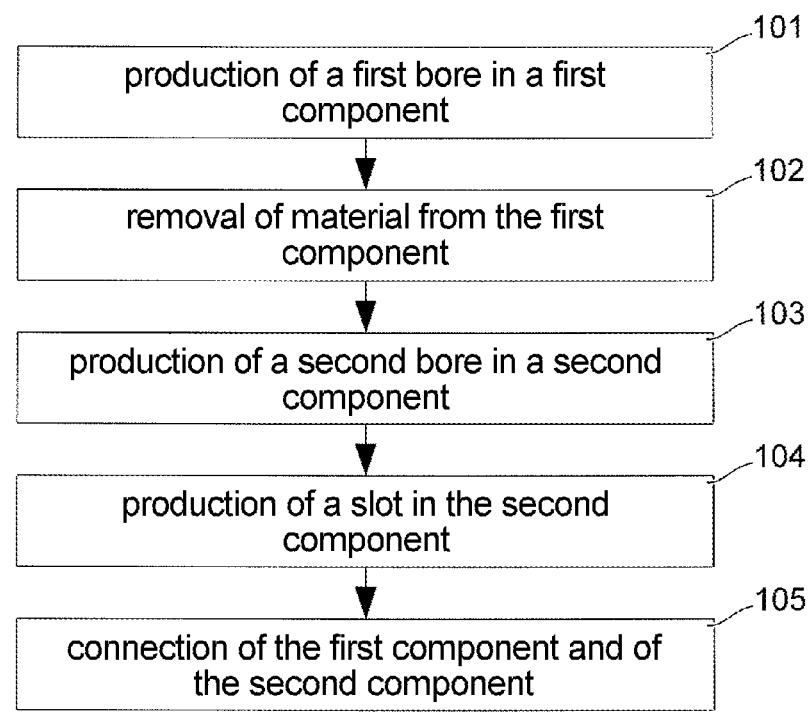
FIG. 11 shows a schematic flow diagram of a method for producing a handling device.

FIG. 11 shows a schematic flow diagram of a number of method steps of a method for producing a handling device. Although it is also possible to produce a handling device that has different features, characteristics or functions from the handling devices illustrated by means of FIGS. 2 to 10 using a method that has the steps illustrated by means of FIG. 11, reference signs from FIGS. 1 to 10 are used by way of example below.

In a first step 101, a first bore 42 is produced, in a first component 30 or in a workpiece from which the first component 30 is formed. At the same time or in the same method step or before or after, a recess 38 for a proximal end 82 of a shank 80 can be produced. The first bore 42 has a cross section which is only insignificantly greater than the cross section of a coupling device 94 at the proximal end 92 of a force transmission device 90, for which the handling device 20 is provided.

In a second step 102, material is removed from the first component 30. In particular, material is removed as far as two parallel flat surfaces 47 in two spatial regions 46 arranged symmetrically with respect to one another and symmetrically with respect to the first bore 42. In particular, the axis 44 of the first bore 42 is arranged parallel to the flat surfaces 47 and in the center between the flat surfaces 47. The distance between the flat surfaces 47 up to which material is removed is less than the diameter of the first bore 42, with the result that the flat surfaces 47 intersect the cross section of the first bore 42. Parts of the inner surface 43 of the first bore 42 are therefore removed during removal 102 of the material. Remaining regions of the inner surface 43 of the first bore 42 form sliding surfaces 32, 34 on parallel and mutually opposite edges of two webs 31, 33, which are delimited by the flat surfaces 47.

In a third step 103, a second bore 62 is produced in a second component 50 or in a workpiece from which the second component 50 is formed. The cross section of the second bore is somewhat larger than the cross section of the coupling device 94 at the proximal end 92 of the force transmission device 90 for which the handling device 20 is provided. For example, the cross section of the second bore 62 in the second component 50 corresponds to the cross section of the first bore 42 in the first component 30.

In a fourth step 104, a slot 52 is produced in the second component 50. The slot 52 is delimited by two parallel flat surfaces 67, which are parallel to the axis 64 of the second bore 62. The axis 64 of the second bore 62 is arranged in the center between the flat surface regions 67 of the slot 52. The spacing between the flat surface regions 67 of the slot 52 is somewhat greater than the spacing between the flat surfaces 47 and the width of the webs 31, 33 on the first component 30. During the production 104 of the slot 52, parts of the inner surface of the second bore 62 in the second component 50 are removed. Remaining regions of the inner surface 63 of the second bore 62 form inner surfaces of two grooves 54 in the otherwise flat surface regions 67 of the slot 52.

In a fifth step 105, the first component 30 and the second component 50 are connected in such a way by a joint that the second component 50 can be pivoted relative to the first component 30 about a pivoting axis 28 which is orthogonal to the axis 44 of the first bore 42 in the first component 30 and orthogonal to the axis 64 of the second bore 62 in the second component 50 and hence both orthogonal to the axis of symmetry of the sliding surfaces 32, 34 on the first component 30 and orthogonal to the axis of symmetry of the grooves 54 in the second component 50.

The sequence of the steps can differ from that illustrated. In particular, the third step 103 and/or the fourth step 104 can be carried out before the first step 101 and/or before the second step 102. The second step 102 can furthermore be carried out before the first step 101, and the fourth step 104 can be carried out before the third step 103.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A handling device for the formation of a disassemblable medical instrument, comprising:
    a first component having a first component step;
    a second component configured to be moved relative to the first component, the second component having a second component step corresponding to the first component step, and the second component step configured to rest against the first component step to form a mechanical stop thereby defining a release position by engagement of the first component step and the second component step;
    a coupling device on the second component, wherein the coupling device is designed and arranged in order to be coupled to a corresponding coupling device at the proximal end of a force transmission device within a working range of positions of the second component, and in order not to be coupled to the corresponding coupling device at the proximal end of the force transmission device in the release position of the second component; and
    a guiding device positioned on the first component for guiding the corresponding coupling device at the proximal end of the force transmission device within an entire transitional range between one end of the working range and the release position of the second component,
    wherein the guiding device comprises a first sliding surface configured on a first web faces a second web, and a second sliding surface configured on the second web faces the first web, and wherein the guiding device configured for guiding the corresponding coupling device at the proximal end of the force transmission device.

2. The handling device according to claim 1, wherein the second component has a slot, in which the first web and the second web on the first component are arranged.

3. The handling device according to claim 2, wherein the coupling device on the second component comprises two parallel and mutually opposite grooves in two mutually opposite walls of the slot.

4. The handling device according to claim 3, wherein the coupling device is designed for coupling to a spherical corresponding coupling device at the proximal end of the force transmission device, a width of the first web and the second web and a width of the slot are each less than the diameter of the spherical corresponding coupling device at the proximal end of the force transmission device for which the handling device is provided.

5. The handling device according to claim 1, wherein the first sliding surface and the second sliding surface have the form of a segment of a lateral surface of a circular cylinder.

6. The handling device according to claim 1, wherein the first sliding surface and the second sliding surface are designed and arranged in order to guide between them the corresponding coupling device at the proximal end of the force transmission device.

7. The handling device according to claim 6, wherein the first sliding surface and the second sliding surface have the form of two segments of a lateral surface of a circular cylinder.

8. The handling device according to claim 1, wherein the second component is pivotable relative to the first component.

9. The handling device according to claim 1, wherein the working range of positions of the second component comprises a first extreme position of the second component relative to the first component, a second extreme position of the second component relative to the first component, and a plurality of positions between the first extreme position and the second extreme position within the working range.

10. A disassemblable medical instrument comprising:
a handling device according to claim 1; and
a shaft, the proximal end of which is connected to or can be connected mechanically in a releasable manner to the handling device,
wherein the force transmission device having the coupling device, corresponding to the coupling device on the second component, at the proximal end of the force transmission device.

* * * * *